(12) United States Patent
Livernois

(10) Patent No.: US 9,707,051 B1
(45) Date of Patent: Jul. 18, 2017

(54) DEPTH LIMITING BUR

(75) Inventor: Melbourne J. Livernois, Cullowhee, NC (US)

(73) Assignee: SS WHITE BURS, INC., Lakewood, NJ (US)

( * ) Notice: Subject to any disclaimer, the term of this patent is extended or adjusted under 35 U.S.C. 154(b) by 506 days.

(21) Appl. No.: 13/232,962

(22) Filed: Sep. 14, 2011

(51) Int. Cl.
*A61C 3/02* (2006.01)

(52) U.S. Cl.
CPC ..................... *A61C 3/02* (2013.01)

(58) Field of Classification Search
CPC ...................................... A61C 3/02
USPC ....... 433/165–166; 175/325.5, 408
See application file for complete search history.

(56) References Cited

U.S. PATENT DOCUMENTS

| | | | | | |
|---|---|---|---|---|---|
| 2,280,927 | A | * | 4/1942 | Phillips | 433/165 |
| 2,453,696 | A | * | 11/1948 | Brooks | 433/165 |
| 3,576,076 | A | * | 4/1971 | Weissman | 433/165 |
| 3,645,642 | A | * | 2/1972 | Koslow | 408/202 |
| 4,010,807 | A | * | 3/1977 | Fischer | 175/325.5 |
| 4,526,542 | A | * | 7/1985 | Kochis | 433/165 |
| 4,787,848 | A | * | 11/1988 | Ross | 433/165 |
| 4,854,871 | A | * | 8/1989 | Weissman | 433/166 |
| 5,201,619 | A | * | 4/1993 | Yodoshi | 409/132 |
| 5,575,650 | A | * | 11/1996 | Niznick et al. | 433/165 |
| 5,839,897 | A | * | 11/1998 | Bordes | 433/165 |
| 5,868,572 | A | * | 2/1999 | Lazzara et al. | 433/173 |
| 5,890,897 | A | * | 4/1999 | Kruger et al. | 433/75 |
| 6,186,788 | B1 | * | 2/2001 | Massad | 433/165 |
| 6,235,035 | B1 | * | 5/2001 | Boukhris | 606/80 |
| 6,319,005 | B1 | * | 11/2001 | Hollander et al. | 433/165 |
| 6,511,322 | B1 | * | 1/2003 | Kometas | 433/166 |
| 6,739,872 | B1 | * | 5/2004 | Turri | 433/75 |
| 7,021,933 | B2 | * | 4/2006 | Caldwell | 433/165 |
| 7,300,341 | B2 | * | 11/2007 | Tetsuka | 451/548 |
| 2002/0172923 | A1 | * | 11/2002 | Strong et al. | 433/165 |
| 2003/0026669 | A1 | * | 2/2003 | Lang et al. | 408/226 |
| 2005/0130103 | A1 | * | 6/2005 | Caldwell | 433/165 |
| 2007/0099150 | A1 | * | 5/2007 | Muller et al. | 433/165 |
| 2007/0238068 | A1 | * | 10/2007 | Comfortes | 433/165 |
| 2009/0162812 | A1 | * | 6/2009 | Harouni | 433/166 |

* cited by examiner

*Primary Examiner* — Cris L Rodriguez
*Assistant Examiner* — Matthew Saunders
(74) *Attorney, Agent, or Firm* — Ice Miller LLP

(57) ABSTRACT

A depth limiting bur is provided. The depth limiting bur can include a cutting head with a diameter of at least two millimeters, a depth cut limiter with a convex surface, and a rod.

7 Claims, 3 Drawing Sheets

DEPTH LIMITING BUR

BACKGROUND OF THE INVENTION

Field of the Invention

The present invention relates to dentistry and more particularly to dental burs in restorative dentistry.

Description of the Related Art

Structural loss in a tooth from dental caries, external trauma, or during tooth preparation can be addressed with dental restoration. Computer-aided design (CAD) and computer-aided manufacturing (CAM) dentistry is an area of dentistry utilizing CAD/CAM technologies to produce different types of dental restorations, including crowns, inlays and onlays, veneers, fixed bridge abutments, and dental implant restorations. The concept of chair side CAD/CAM restoration differs from conventional dentistry in that the prosthesis is typically luted or bonded in place the same day, whereas conventional dental prosthesis of larger size such as crowns have temporaries placed for several weeks while a dental laboratory produces the restoration offsite.

Typically CAD/CAM restorations are milled from solid blocks of composite resin or porcelain matching the shade of the restored tooth. Before the restoration is milled, a tooth must be first prepared for the replacement with a restorative material. The process of preparation usually involves cutting the tooth to make space for the planned restorative material and to remove any dental decay or portion of the tooth that is structurally unsound. The tooth must be reduced enough to allow the ceramic material to be thick enough when chewed on by the teeth in the opposing arch to match a minimum depth as recommended by a manufacturer. After the problem is removed from the disease tooth, proper medications and base materials are placed and shaped and an impression is taken of the resulting preparation. The impression can be made with an elastic material or with a 3-D image. When utilizing CAD-CAM technologies, the data that forms the images is used by computer software to create a virtual replacement of the natural tooth morphology. The software then sends the virtual data to a milling chamber where the dental restoration is carved out of the restorative material. The dental restoration can be further adjusted in the patient's mouth, polished, and then bonded in place.

Of note, the software of the CAD-CAM equipment assumes that a dentist removes enough tooth structure to meet the recommendations of a manufacturer for the selected type of restoration and restorative ceramics. Since the virtual ceramic design must fit between the top of the preparation and the opposing teeth, the dentist must check the depth of the ceramic during the virtual design process or use cutting tools, which can give exact, preselected depth cuts. When the dentist does not have a measured cutting tool, he or she must check the depth after the impression and the design has been completed. If depth is not adequate, the dentist must return to the mouth and take more tooth off.

Also of note, in the method advocated for tooth preparation, the width and depth of an initial central-fossa cut during tooth preparation depends on the material to be used. Most ceramic manufacturers recommend a minimum cut of two millimeter in width for all ceramics. The recommended depth of a cut varies on the material used. For instance, if a feldspathic ceramic block (also known as feldspathic porcelain) is used, the manufacturers recommend a cut of two millimeter in depth; for lithium disilicate blocks a one millimeter depth for inlays is recommended, but a one and half millimeter depth cut for restorative work elsewhere; for leucite reinforced blocks a one and half millimeter depth cut is recommended; and, for composite blocks, such as a composite of ceramic particles and BISGMA polymer, a one millimeter depth cut is recommended. Of further note, the depth of a cut is measured from the central-fossa (the "valley" between the lingual cusp incline and the buccal cusp incline) to the surface of the remaining dentin. The central-fossa is a line that extends from the end of the triangular ridge area of a tooth. It goes up and down (gingivo-occlusally) in vertical height as the topography of a tooth changes. Of even further note, because CAD/CAM software re-establishes this central-fossa line which goes up and down following the cusp inclines of a tooth, if the cut is not appropriately sized vertically, when the image is taken, the resulting milled product can be too thin in some areas and thicker in others, thus the ceramic of the restoration would not have the required physical properties, which could lead to the fracturing of the ceramic requiring that the entire procedure be redone.

BRIEF SUMMARY OF THE INVENTION

Embodiments of the present invention address deficiencies of the art in respect to dental limiting burs and provide a novel and non-obvious apparatus for limiting the width and depth of a cut. In an embodiment of the invention, a depth limiting bur can include a depth cut limiter with a convex surface, a cutting head with a diameter of at least two millimeters and disposed at a distal end of the depth limiter, and a rod affixed to the depth cut limiter at an opposite end of the depth cut limiter from the cutting head.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

Embodiments of the invention provide for a depth limiting bur. The depth limiting bur can include a cutting head that has a diameter of two millimeters disposed at a distal end of a depth cut limiter. In this way, the depth limiting bur can initially create a two millimeter width cut as recommended by all ceramic manufactures when ceramics are used as the restorative material in restorative dentistry, including all ceramic, CAD/CAM designed and milled, indirect dental restorations as well as restorations that require a predetermined depth of restorative material to replace tooth structure. By initially creating the two millimeter width, a dentist is not required to widen the cut, which prevents uncontrolled cuts.

The depth cut limiter can have a convex surface. Of note, when the convex surface contacts the cusp inclines of the molar or bicuspid (the lingual cusp incline and the buccal cusp incline) the cutting head is restrained, thus prohibiting additional depth cutting. In this way, the depth of the cut is limited allowing a more accurate depth cut. In addition, if a dentist does not have a tool capable of creating depth cuts, he or she must check the depth of a cut after an impression and after a CAD/CAM design has been completed. If the depth is not adequate, the dentist must return to the mouth to take more tooth off, if not the resulting restoration would be too thin, thus subject to ceramic fracture and restoration failure. The depth cut limiter can be affixed to a rod at an opposite end of the depth cut limiter from the cutting head. Of note, the rod of the depth limiting bur can be attached to a dental tool, such as an air turbine, a high-speed, geared electric motor, or other dental handpiece, which can rotate the bur, for instance between one hundred thousand and four hundred thousand revolutions per minute.

Figure 1A:
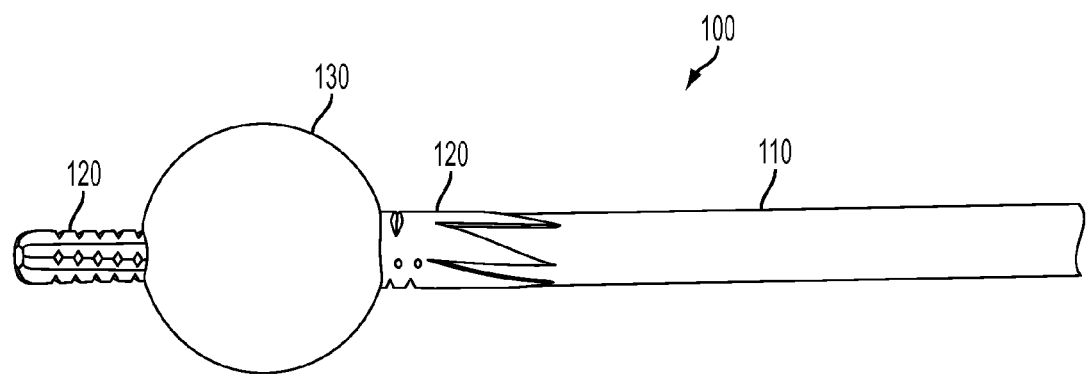
FIG. 1A is a view of an embodiment of a depth limiting bur in accordance with this invention.
Figure 1B:
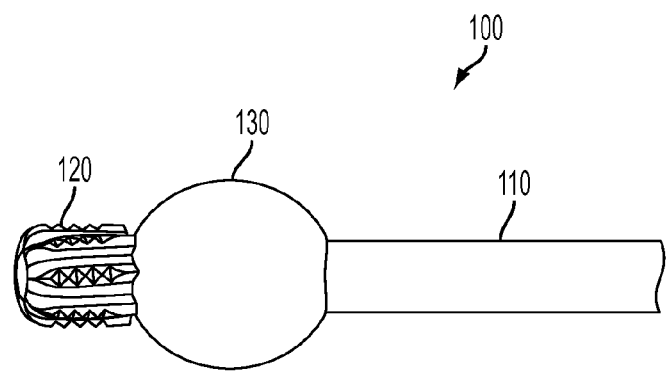
FIG. 1B is a view of an embodiment of a depth limiting bur in accordance with this invention.

In further illustration, FIG. 1A and FIG. 1B are views of different embodiments of a depth limiting bur 100 in accordance with this invention. In an embodiment, the depth limiting bur 100 can include a rod 110 coupled to a depth cut limiter 130 at an opposite end of the depth cut limiter from a cutting head 120. The rod 110 can be made of any material now known or later developed, including but not limited to metal, such as stainless steal and tungsten carbide. The rod 110 can vary in both diameter and length. In addition, the rod 110 is not limited to a specific cross section; for example, in one embodiment, the rod 110 can have a circular cross section, and in a different embodiment, the rod can have a square cross section. For instance, the rod 110 can have a circular cross section that can vary in diameter from one millimeter to four millimeter and vary in length from fourteen millimeters to twenty eight millimeters. The rod 110 can be configured at one end to fit into a dental handpiece, including but not limited to an air turbine and a high speed, geared electric motor dental handpiece. In one embodiment, the rod 110 can be configured to be held by a friction-grip chuck, which can then be attached to a dental handpiece; the dental handpiece rotates the depth limiting bur 100. Of note, in an embodiment, the high-speed, geared electric motor can rotate the depth limiting bur 100 one hundred thousand to four hundred thousand revolutions per minute. The rod 110 can be manufactured by any process now known or later developed, including but not limited to casting, rolling, forging, and extrusion. In one embodiment, the rod 110 can be an extruded wire.

The depth cut limiter 130 can be affixed to the rod 110 in a variety of ways, including but not limited to welding, staking, and threading. Of note, in one embodiment, the depth cut limiter 130 can have an aperture in which the rod 110 can pass through; the rod 110 and the depth cut limiter 130 can then be coupled to one another, though any method now known or later developed, including but not limited to welding, staking, and threading, where the rod 110 can have an external thread and the depth cut limiter 130 can have an internal thread. In another embodiment, the depth cut limiter 130 and the rod 110 can be manufactured as a singular component. The depth cut limiter 130 can be a variety of shapes, including but not limited to elliptical and spherical in shape, provided the depth cut limiter 130 has a convex surface. In this way, the convex surface of the depth cut limiter 130, being wider than the shaft 110, can contact the lingual cusp incline and the buccal cusp incline of a tooth, such as a molar or bicuspid tooth, preventing the depth limiting bur 100 from cutting too deep. In other words, the convex nature of the depth cut limiter 130 restrains the depth of the cut created by the depth limiting bur 100. In addition, the convex nature of the depth cut limiter 130 is less prone to lateral rocking as other shaped devices, such as a conical limiter or a flat sided, angular limiter. Of note, the convex surface of the depth cut limiter 130 provides a geometrically more accurate guide along the lingual cusp incline and the buccal cusp incline. Thus, the depth of the depth limiting bur 110 can be more accurate than other shaped devices. The depth cut limiter 130 can vary in size, for example from about two millimeters to about five millimeters, but in an embodiment, the depth cut limiter 130 can have a diameter of three and one-half millimeters. The depth cut limiter can be formed of any material now known or later developed, including but not limited to metal, such as stainless steal, tungsten carbide, or any metal alloy. The depth cut limiter 130 can be manufactured by any process now known or later developed, including but not limited to casting, such as hollow casting, rolling, forging, and extrusion.

The depth cut limiter 130 can further be coupled to a cutting head 120 with the cutting head 120 disposed at a distal end of the depth cut limiter 130. Of note, the depth cut limiter 130 can be positioned in a variety of locations; for example, the depth cut limiter 130 can be sandwiched between the cutting head 120 and the rod 110; the depth cut limiter 130 can be affixed to the rod 110 with the rod 110 coupled to the cutting head 120; or, the depth cut limiter 130 can be affixed to the cutting head 120 with the cutting head 120 affixed to the rod 110. Of further note, optionally, the cutting head 120 and the depth cut can be manufactured as one piece; the cutting head 120, the depth cut limiter 130, and the rod 110 can be manufactured as one piece; or, the rod 110 and the depth cut limiter 130 can each be manufactured as one piece. The cutting head 120 can be made of any material now known or later developed, including diamond, metal, such as stainless steel, tungsten carbide, or metal alloy.

In one embodiment, the cutting head 120 is made of tungsten carbide, which allows for both a smoother cut and easier rinse off of tooth particles. In this way, increased bond strength between the restorative material and the tooth can be achieved with a tungsten carbide cutting head 120 as opposed to using a cutting head made of another material, such as a cutting head with a diamond-coated abrasive. Increased bond strength is due to the fact that the "smear layer" of tooth grindings does not get imbedded in the tooth surface with a tungsten carbide cutting head 120 as it does with a diamond-coated abrasive cutting head. Of further note, if the dentist chooses to utilize a "single bottle" or a sixth or seventh generation bonding primer, the "smear layer" can cause the bond between the adhesive resin cement and the tooth to be weaker. This "smear layer" bonding can additionally lead to latent sensitivity and debonding, which can cause fractures and failed restorations. Of note, adhesive failure between the tooth and the adhesive resin cement usually occurs because the dentin bonding agent breaks loose.

In addition, the cutting head 120 can be at least two millimeters in diameter; in this way, a cut of two millimeters can be achieved without moving the depth limiting bur to widen the cut. Two millimeters is the minimum width cut the ceramic manufacturers recommend in order to provide adequate bulk to prevent material failure due to flexure. Of note, the depth of the cut depends on the material being used; for example, for feldspathic porcelain a depth of two millimeters is recommended; for lithium disilicate a one millimeter depth cut for inlays is recommended, but a one and half millimeter depth cut elsewhere; for leucite reinforced blocks a one and half millimeter depth cut is recommended; and, for composite blocks, such as a composite of ceramic particles and BISGMA polymer, a one millimeter depth cut is recommended. In addition, the cutting head 120 can have a tip of any shape, including but not limited to being rounded.

Upon attachment of the depth limiting bur 100 with a cutting head 120, a depth cut limiter 130, and a rod 110 to a powered-on, dental handpiece, the rotating bur 100 can be pressed into a molar or bicuspid to the depth allowed by the depth cut limiter 130. After powering on the dental handpiece, a cut of desired depth and width can be created. In this way, a tooth, such as a molar, can be prepared with a central-fossa area of correct depth for all restorative ceramic materials.

Figure 2A:
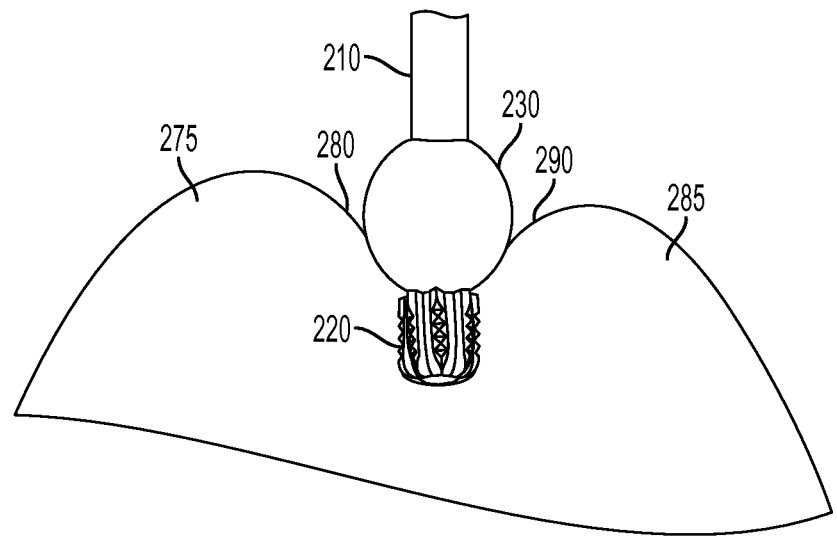
FIG. 2A is a view of a depth limiting bur making contact with a molar or bicuspid tooth (in cross section) in accordance with an embodiment of this invention.
Figure 2B:
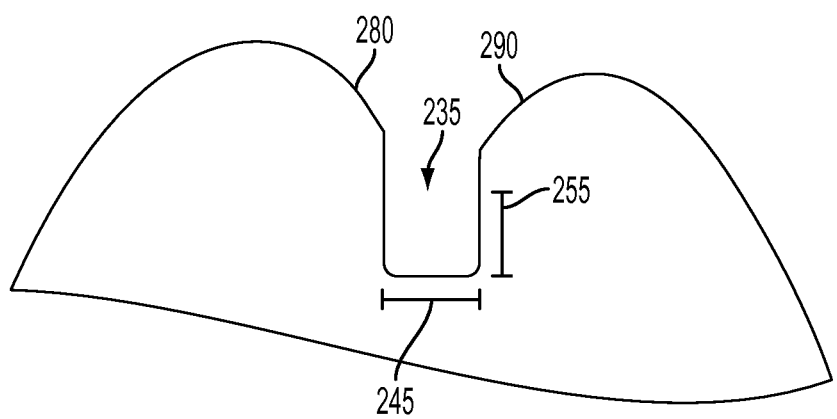
FIG. 2B is a view of the cut made with a depth limiting bur in accordance with an embodiment of this invention; and, FIG. 3 shows a prior art depth cutter being moved in multiple directions in order to achieve the recommended cut width required for use with ceramic restorative materials.

In further illustration, FIG. 2A is a view of a depth limiting bur making contact with a molar (in cross section) in accordance with an embodiment of this invention. A depth limiting bur with a rod 210 affixed to a depth cut limiter 230 at an opposite end of the depth cut limiter from a cutting head 220 can be rotated by a dental handpiece and pressed into a molar to the depth allowed by the depth cut limiter 230. As the rotating, depth limiting bur is plunged into the molar, the depth limiting bur creates a cut having a depth 255 and width 245, as seen in FIG. 2B. The width 245 of the cut is based on the diameter of the cutting head 220, which is at least two millimeters. Two millimeters is the minimum recommended width by ceramic manufacturers.

The depth 255 of a cut is determined by the length of the cutting head 220 (the distance from the depth cut limiter 230 and the end of the cutting head 220) as well as contact of the depth cut limiter 230 with the lingual cusp incline 280 of the lingual cusp 275 and the buccal cusp incline 290 of the buccal cusp 285, because once the depth limiting bur contacts the inclines 280, 290 the bur can no longer make a deeper cut. Of note, during manufacturing, the position of the depth cut limiter 230 can be varied, thus allowing for changes in length to the cutting head 220. In this way, the cutting head 220 can vary in length from about one quarter of a millimeter to three and half millimeters, allowing the depth 255 of a cut to vary from about one quarter of a millimeter to about three and half millimeters, allowing the depth limiting bur to be used in any application requiring definitive amounts of tooth tissue reduction, including but not limited to crowns, inlays and onlays, veneers, fixed bridges abutments, and dental implant restorations.

Manufacturers of the materials used in restorative dentistry provide recommend cut depths 255 depending on the material being used. Of note, the depth 255 of a cut is measured from the central-fossa 235 (the intersection of the lingual cusp incline 280 and the buccal cusp incline 290) to the bottom of the cut (gingival direction). For instance, if feldspathic porcelain is used, the manufacturer recommends a depth 255 of two millimeters. In practice, to reach a depth 255 of two millimeters, measured from the central-fossa 235, the length of the cutting head 220 would need to extend about two and three-tenths millimeters from the distal end of the depth cut limiter 230 for a tooth having a cusp incline of about thirty degrees based on geometric analysis. For a tooth having a cusp incline of about thirty five degrees, the length of the cutting head 220 would need to extend about two and four-tenths millimeters from the distal end of the depth cut limiter 230, and for a tooth having a cusp incline of about twenty degrees the length of the cutting head would need to extend about two and two-tenths millimeters from the distal end of the depth cut limiter 230.

Of note, for an unworn, young tooth, the cusp inclines, which includes the lingual cusp incline 280 and the buccal cusp incline 290, are generally each between about twenty degrees and thirty five degrees as measured from the central-fossa 235. But the cusp inclines can vary with age and wear as well as be dependent on the intercuspal distance (the width between the apex of the lingual cusp and the buccal cusp). Of further note, the central-fossa 235 is the "valley" between the lingual cusp incline 280 and the buccal cusp incline 290. The central-fossa 235 is a line that extends from the end of the triangular ridge area of a tooth; it goes up and down in vertical (gingival-occlusal) height.

Figure 3:
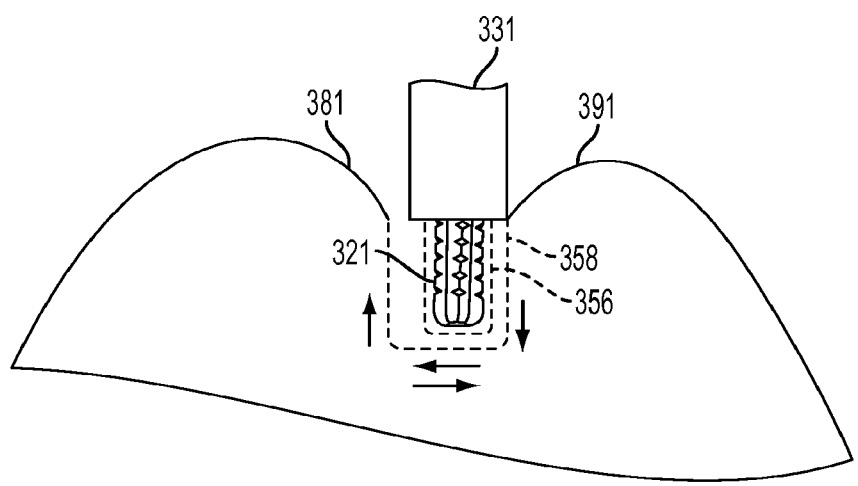

In further illustration, FIG. 3 shows a prior art depth cutter with a straight limiter 331 and a cutting head 321 comprising a diameter of less than two millimeters being moved in multiple directions in order to achieve the recommended cut width of two millimeters for use with milled ceramic restorative materials. In practice with a prior art depth cutter, the dentist performing restorative dentistry must move the cutter from side to side and up and down after the initial cut 356, as shown by the arrows in FIG. 3, in order to widen the cut to the recommended width 358, for instance two millimeters for feldspathic porcelain, because the initial cut 356 is less than two millimeters in width. As a result of the widening, the straight limiter 331 must fall off the tooth structure (the buccal cusp incline 391 or the lingual cusp incline 381, depending on which direction the dentist moves the prior art depth cutter), which was originally limiting the depth. As illustrated in FIG. 3, the straight limiter 331 looses contact with the buccal cusp incline 391 and travels along the lingual cusp incline 381 to widen the cut. When the prior art depth cutter is moved back to the center (to the central-fossa), the lateral contact of the straight limiter 331 with both the lingual cusp incline 381 and the buccal cusp incline 391 no longer functions properly, because the tooth has been cut away. As a result of the widening, the prior art depth cutter allows deeper cuts then the straight limiter 331 would have originally allowed, causing inaccurate depth limiting as well as deeper cuts than desired.

Having thus described the invention of the present application in detail and by reference to embodiments thereof, it will be apparent that modifications and variations are possible without departing from the scope of the invention defined in the appended claims as follows:

I claim:

1. A depth limiting bur for removing tooth material in preparation for applying a dental restoration comprising:
   a depth cut limiter comprising a convex surface and having a depth cut limiter diameter;
   a cutting head having a length, comprising a maximum diameter of at least two millimeters and extending immediately from the convex surface at a distal end of the depth cut limiter, the maximum diameter being less than that of the depth cut limiter diameter, and said cutting head having a plurality of blades extending from the surface of the cutting head along the length of the cutting head; and a rod affixed to the depth cut limiter at an opposite end of the depth cut limiter from the cutting head, said rod having a diameter that is substantially the same as the maximum diameter of the cutting head, said rod having a length which is greater than the length of the cutting head, said rod adapted to be attached to a rotating dental handpiece.

2. The depth limiting bur of claim 1, wherein the cutting head is formed of tungsten carbide metal.

3. The depth limiting bur of claim 1, wherein the depth cut limiter is spherical in shape.

4. The depth limiting bur of claim 1, wherein the cutting head length is two millimeters.

5. The depth limiting bur of claim 1, wherein the cutting head length is one and a half millimeters.

6. The depth limiting bur of claim 1, wherein the cutting head length is one millimeter.

7. The depth limiting bur of claim 1, wherein the blades are serrated.

* * * * *